(12) United States Patent
Takahashi

(10) Patent No.: US 6,319,198 B1
(45) Date of Patent: Nov. 20, 2001

(54) ELECTRONIC ENDOSCOPE

(75) Inventor: Tadashi Takahashi, Saitama (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/428,467

(22) Filed: Oct. 28, 1999

(30) Foreign Application Priority Data

Oct. 29, 1998 (JP) .................................................. 10-308348

(51) Int. Cl.$^7$ ....................................................... A01B 1/06
(52) U.S. Cl. ............................ 600/180; 600/181; 348/69; 362/574
(58) Field of Search .................................... 600/178, 180, 600/181; 346/68, 64, 363, 364; 362/574

(56) References Cited

U.S. PATENT DOCUMENTS 4,834,071 * 5/1989 Hosoi et al. .......................... 600/180
4,868,645 9/1989 Kobayashi .

FOREIGN PATENT DOCUMENTS

| 5-328364 | 12/1993 | (JP) . | |
|---|---|---|---|
| 6-139341 | 5/1994 | (JP) . | |
| 6-153209 | 5/1994 | (JP) . | |
| 8-313826 | 11/1996 | (JP) . | |
| 8-62511 | * 3/1996 | (JP) | ................................. A61B/1/00 |

* cited by examiner

Primary Examiner—John Mulcahy
(74) Attorney, Agent, or Firm—Greenblum & Bernstein, P.L.C.

(57) ABSTRACT

In an electronic endoscope, a video-scope has an image sensor for photographing an object image and a light guide for guiding light toward an object. A video-processor has a light source, a stop, a signal conversion circuit, a histogram processing circuit, and a CPU. When the video-scope is connected to the video-processor, light emitted from the light source is guided by the light guide and radiates from a distal end of the light guide, so that an object image is formed on the image sensor. The object image is then converted into the image-pixel signals. Further, a representative value, which relates to a brightness of the object image, is calculated on the basis of the image-pixel signals through the signal conversion circuit, the histogram processing circuit, and the CPU.

Then, a control of light radiating from the distal end of the light guide is performed at regular time-intervals. Namely, the stop is controlled such that the brightness of the object image is proper. In this case, when the representative value is not newly calculated, the stop is driven.

11 Claims, 4 Drawing Sheets

ELECTRONIC ENDOSCOPE

BACKGROUND OF THE INVENTION

1. Field of the Invention

This invention relates to an electronic endoscope for displaying a body-cavity image on a TV monitor, which comprises a video-scope having an image sensor and a video-processor. In particular, this invention relates to a control of a brightness of an object image.

2. Description of the Related Art

In the electronic endoscope, the video-scope includes an optical light guide extended therethrough, which is formed as a bundle of optical fibers. On the other hand, the video-processor includes a light source, such as a halogen lamp. When the video-scope is connected to the video-processor, a proximal end of the optical light guide is optically connected to the light source. Thus, an object to be photographed is illuminated by light radiating from a distal end of the optical light guide, and an object image is formed on the image sensor provided at the distal end of the video-scope. Then, the object image, formed on the image sensor, is converted into analog image-pixel signals by photoelectric conversion.

The analog image-pixel signals are fed to the video-processor and are suitably processed, so that video signals are generated., The video signals are then output to a TV monitor. Thus, an body-cavity image (for example, a stomach image) is displayed on the monitor.

In general, to maintain a proper brightness of the object image displayed on the monitor, a quantity of light radiating from the distal end of the optical light guide should be regulated. Conventionally, for a regulation of the quantity of light, a stop (diaphragm) provided between the light source and the proximal end of the light guide is controlled, such that the brightness of the object image is maintained at a constant level.

In this case, luminance signals are generated from one frame's worth of the analog image-pixel signals, which are successively extracted from the image sensor, and an average luminance value is successively calculated on the basis of the luminance signals. Then, the stop is controlled on the basis of the difference between the average luminance value and a predetermined reference value. According to the image-pixel signals successively read from the image sensor, the regulation of the quantity of light is successively performed i.e. at regular time-intervals.

In this way, by regulating the quantity of light automatically, the brightness of the object image is maintained at a proper level. Thus, on the monitor, the object image is always displayed with a proper brightness However, in such an automatic regulation of the quantity of light, occasionally the average luminance value can not be calculated. For example, when the average luminance value is calculated by a histogram processing, an imperfect histogram-data, that is, a histogram-data not corresponding to one frame's worth of the object image is occasionally generated. In this case, as the average luminance value is not calculated, the stop is controlled on the basis of a preceding average luminance value, which is calculated from the preceding calculation.

However, the brightness of the object image formed on the image sensor has been already corrected, and the stop is driven in error, so that a hunting-situation, in which the stop does not converge to a proper position for a long time, occurs.

On the other hand, if the regulation of the quantity of light is performed at longer time-intervals in order to solve the above problems, the stop can not be rapidly controlled when the brightness of the object image changes considerably.

SUMMARY OF THE INVENTION

Therefore, an object of the present invention is to provide an electronic endoscope that can rapidly adjust the brightness of the object image by controlling the stop, without causing the hunting-situation.

An electronic endoscope according to the present invention comprises a video-scope having an image sensor and a video-processor. Further, the electronic endoscope comprises a light source, a stop, luminance generator, a calculator, a light-controller, and determiner. The image sensor on which an object image is formed is provided at a distal end of the video-scope. The video-processor, to which a proximal end of the video-scope is connected, processes image-pixel signals corresponding to the object image, successively read from the image sensor. The light source is provided in the video-processor such that light, emitted from the light source, is guided through the video-scope and radiates from the distal end of the video-scope. The stop is provided between the light source and the proximal end of the video-scope for adjusting a quantity of light radiating from the distal end of the video-scope. The luminance generator successively generates luminance signals from the image-pixel signals. The calculator successively calculates a representative value, associated with a brightness of the object image, on the basis of the luminance signals. The light-controller adjusts the brightness of the object image at regular time-intervals, by controlling the stop on the basis of the representative value and a predetermined reference value. The determiner determines whether the representative value coincides with a preceding representative value from the preceding calculation. Then, when the representative value does not coincide with the preceding representative value, the light-controller drive the stop, and when the representative value coincides with the preceding representative value, the light-controller does not drive the stop.

BRIEF DESCRIPTION OF THE DRAWINGS

The present invention will be better understood from the description of the preferred embodiments of the invention set forth below together with the accompanying drawings, in which.

DESCRIPTION OF THE PREFERRED EMBODIMENT

Hereinafter, the preferred embodiment of the present invention is described with reference to the attached drawings.

Figure 1:
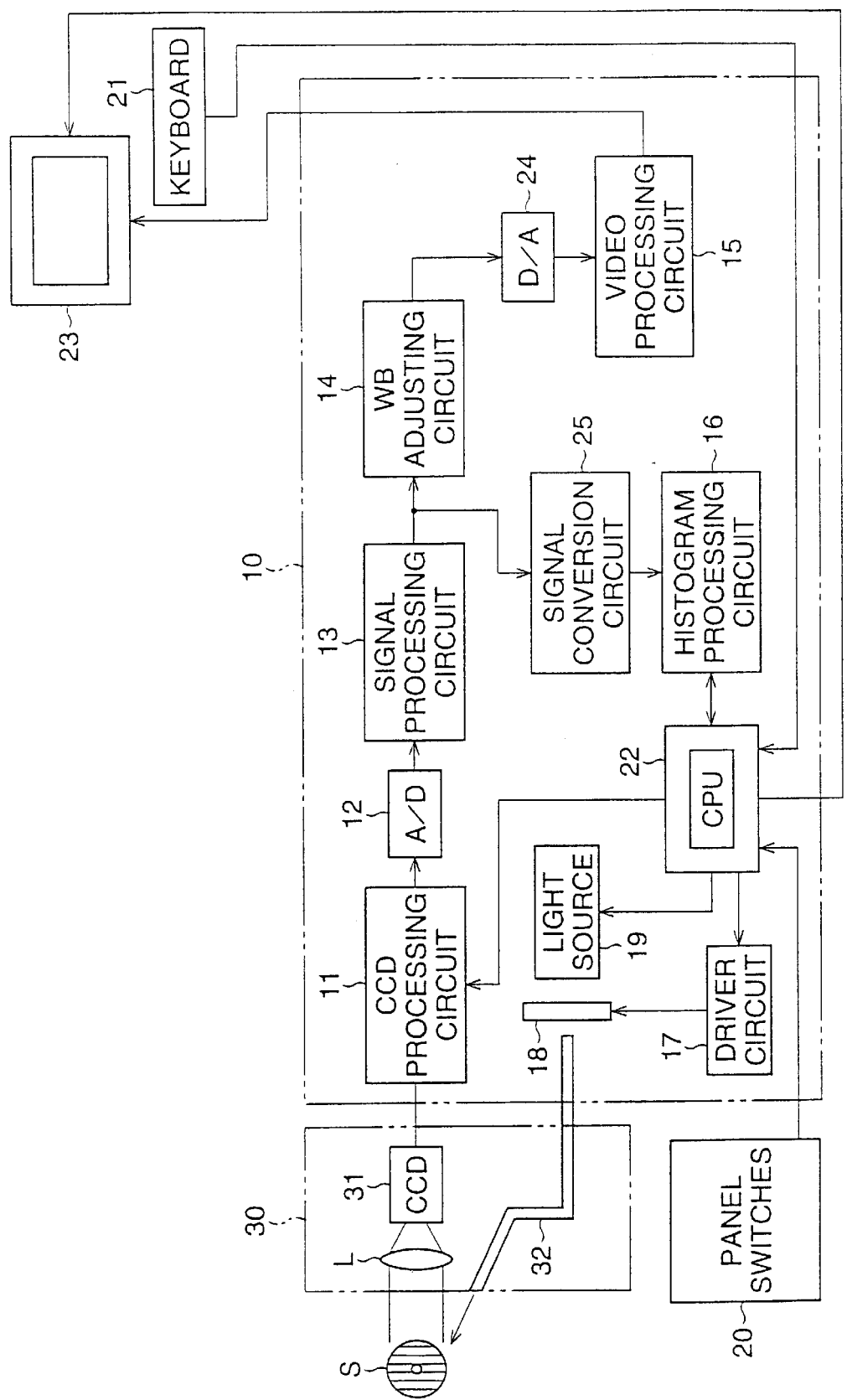
FIG. 1 is a block diagram showing an electronic endoscope of an embodiment of the present invention.

FIG. 1 is a block diagram of an electronic endoscope of the embodiment. This endoscope is used when an operation, an inspection or a treatment regarding an organ, such as a stomach, is performed.

The electronic endoscope comprises a video-processor 10 and a video-scope 30. The video-scope 30 is a flexible conduit, and is detachably connected to the video-processor 10. During an operation or the like, a proximal end of the video-scope 30 is connected to the video-processor 10, and the video-scope 30 is inserted into the body-cavity. Note that, in this embodiment, NTSC Video Standard is applied as a color-television method.

The video-scope 30 includes a light guide 32 extended therethrough, formed as a bundle of optical fibers. When the proximal end of the video-scope 30 is connected to the video-processor 10, the proximal end of the light guide 32 is optically connected to a light source 19, such as a halogen lamp, provided in the video-processor 10. Thus, light, emitted from the light source 19, is directed to the proximal end of the light guide 32, and then radiates from the distal end of the light guide 32 toward an object S.

A stop (diaphragm) 18 is provided between the light source 19 and the proximal end of the light guide 32, and is driven by a stepping motor (not shown), which rotates by a driving-signal output from a driver circuit 17. The stop 18 is used for adjusting a quantity of light directed from the light source 19 to the proximal end of the light guide 32, and therefore adjusting a quantity of the illuminating-light radiating from the distal end of the light guide 32.

A CCD (Charged-Couple-Device) 31, which is an image sensor, is provided at the distal end of the video-scope 30. When the object S is illuminated by the illuminating-light, light reflected from the object S is focused on the CCD 31 via an optical lens L, so that the object image is formed on the CCD 31.

Photoelectric conversion devices (not shown) are provided on the CCD 31, and red (R), green (G), and blue (B) color mosaic-filter elements are provided in front of the photoelectric conversion devices. The object image, formed on the CCD 31, is converted into electrical image-pixel signals corresponding to predetermined colors by the photoelectric conversion devices. These analog image-pixel signals, corresponding to one frame worth, are then successively read from the CCD 31 to a CCD processing circuit 11. Namely, the object image is scanned. In the case of the NTSC method, the analog image-pixel signals are scanned at regular time-intervals of 1/30 sec.

In the CCD processing circuit 11, one frame worth of the analog image-pixel signals, output from the CCD 31 in order, is separated into analog image-pixel signals corresponding to the red R, analog image-pixel signals corresponding to green G, analog image-pixel signals corresponding to blue B. Then, the analog image-pixel signals, corresponding to each color (R, G, B), are amplified and fed to an A/D converter 12, and are converted into digital image-pixel signals, respectively. The digital image-pixel signals, corresponding to each color, are output to a signal processing circuit 13.

In the signal processing circuit 13, the digital image-pixel signals are subjected to various image-processes, such as a reset noise reduction and gamma-correction and etc., and are then output to both a signal conversion circuit 25 and a white-balance adjusting circuit 14.

In the signal conversion circuit 25, luminance signals of one frame are successively generated on the basis of the digital image-pixel signals, and fed to a histogram processing circuit 16. In the histogram processing circuit 16, the luminance signals are written, and subjected to a histogram processing, so that histogram-data are generated. Then, the histogram-data are read from the histogram processing circuit 16 by a CPU (Central Processing Unit) 22. Note that the electronic endoscope is controlled by the CPU 22.

In the CPU 22, a representative value, as described later, is calculated on the basis of the histogram-data and then the representative value is compared with a reference value stored in a memory (not shown). On the basis of a difference between the reference value and the representative value, a control-signal is fed from the CPU 22 to the driver circuit 17, so that the stop 18 is driven. Thus, the quantity of the illuminating-light radiating from the distal end of the light guide 32 is regulated.

On the other hand, in the white balance circuit 14, the digital image-pixel signals are subjected to a white balance adjustment processing. In this embodiment, the digital image-pixel signals are adjusted such that the ratio of R, G, B signals is respectively "1:1:1" when a white object is photographed by the video-scope 30. After the white balance adjustment processing is performed, the digital image-pixel signals are fed to a D/A converter 24.

In the D/A converter 24, the digital image-pixel signals are converted into analog image-pixel signals, and then fed to a video processing circuit 15. In the video processing circuit 15, the analog image-pixel signals are converted into the video signals, such as NTSC signals, and then output to a monitor 23. Therefore, one frame worth of the video signals are successively output to the monitor 23 at regular time-intervals of 1/30 sec, thus, the object image is displayed on the monitor 23, as a moving picture.

When panel switches 20 are operated by an operator to set a level of a brightness of the light source 19 and so on, a operation-signal is input to the CPU 22, thus the brightness of the light source 19 is set. Similarly, when a keyboard 21 is operated, the operation-signal is input to the CPU 22. Thus, for example, a picture on the monitor 23 is changed.

Figure 2:
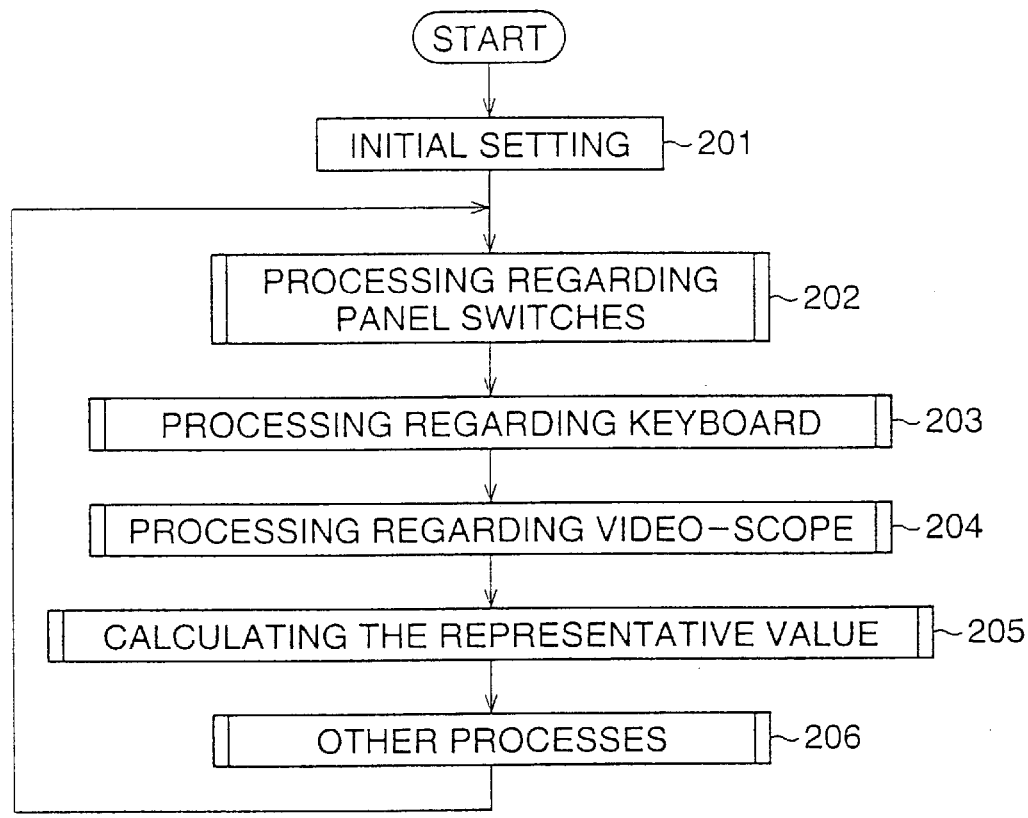
FIG. 2 is a flowchart showing a main routine regarding total operations of the electronic endoscope.

FIG. 2 is a flowchart showing a main routine regarding operations of the electronic endoscope as a whole. When an electric power is ON, the main routine is started.

In Step 201, the stop 18, the light source 19, and etc., are set to an initial setting, respectively. For example, the stop 18 is set to an initial position.

In Step 202, a level of the brightness of the light source 19 is determined in accordance with the operation of the panel switches 20. In Step 203, the picture on the monitor 23 is changed in accordance with an operation of the keyboard 21.

In Step 204, processing regarding the video-scope 30 is performed. For example, a scope-name of the video-scope 30 is displayed on the monitor 23 when the video-scope 30 is newly connected to the video-processor 10.

In Step 205, a representative value is calculated on the basis of the histogram-data. In Step 206, other processes are performed. For example, a real-time is displayed on the monitor 23.

These operations of the electronic endoscope are executed until the electric power is turned OFF. In each Step, a subroutine is respectively performed. Note that, when the keyboard 21 is not operated, Step 203 is not executed, and the process goes to next Step 204. Similarly, when the panel switches 20 are not operated, the process skips step 202 and goes to Step 203.

Figure 3:
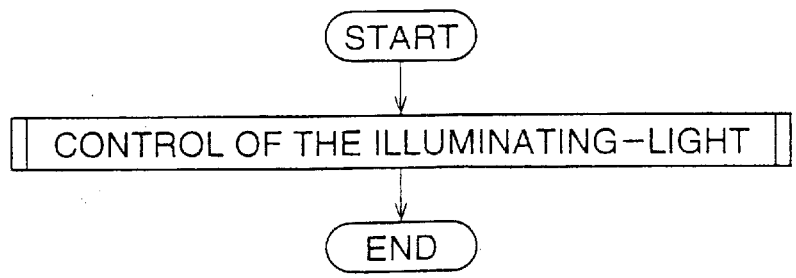
FIG. 3 is a view showing an interrupt processing.

FIG. 3 is a routine showing an interrupt processing for a control of the illuminating-light, as described later. This interrupt processing interrupts the operations of the electronic endoscope shown in FIG. 2, and is performed at time-intervals of 1/30 sec to correspond to a period of scanning one frame of the object image formed on the CCD 31.

Figure 4:
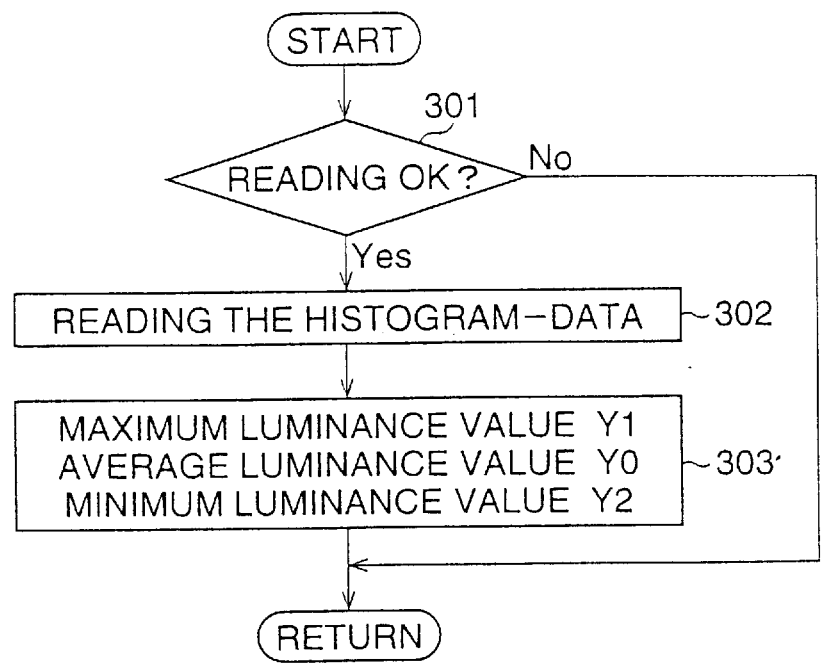
FIG. 4 is a view showing a subroutine of Step 205 shown in FIG. 2

FIG. 4 is a subroutine of Step 205 shown in FIG. 2. In one frame worth of the luminance signals, the range of each luminance value Y, corresponding to each pixel on the CCD 31, is from 0 to 255.

In Step 301, it is determined whether or not a reading of the histogram-data from the histogram processing circuit 16 is possible. When it is impossible to read the histogram-data from the histogram processing circuit 16, the processing of Step 302 and 303 is not executed. On the other hand, when it is possible to read the histogram-data from the histogram processing circuit 16, the process goes to Step 302. Note that, when the histogram-data corresponding to one frame worth of the luminance signals are not generated or the luminance signals have not been written in the histogram processing circuit 16, it is impossible to read the histogram-data.

In Step 302, the histogram-data corresponding to one frame worth of the object image are read and then fed to the CPU 22.

Figure 5:
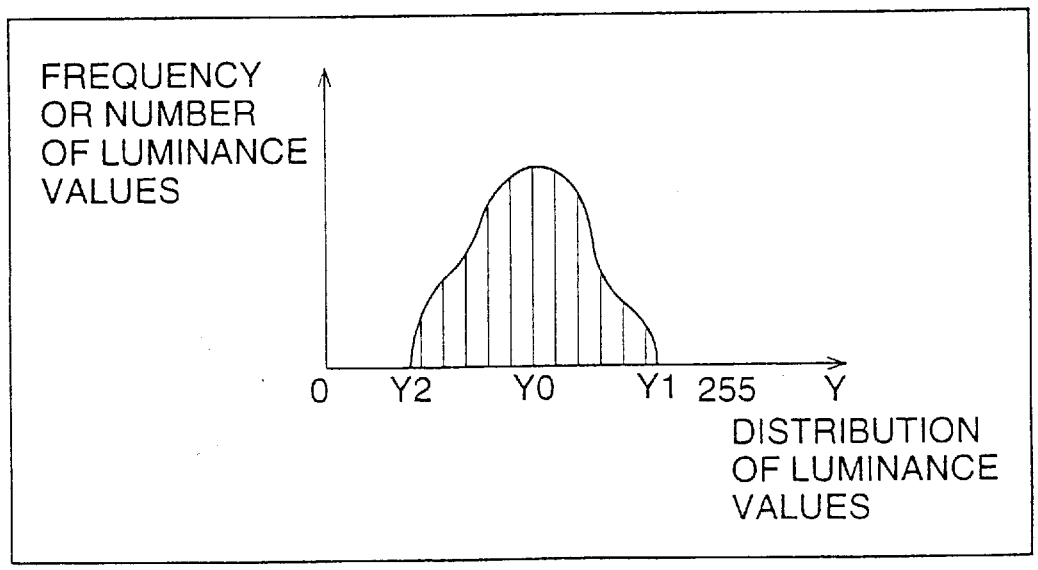
FIG. 5 is a graph showing histogram-data.

FIG. 5 is a view showing the histogram-data. In the histogram-data, a horizontal direction represents a distribution of luminance values Y included in one frame, and a vertical direction represents a frequency or number of the luminance values Y.

In Step 303 shown in FIG. 4, the representative value is calculated on the basis of the histogram-data. The representative value is composed of a maximum luminance value Y1, an average luminance value Y0, and a minimum luminance value Y2. The maximum luminance value Y1, the average luminance value Y0, and the minimum luminance value Y2 represent a maximum value, an average value, and a minimum value in one frame worth of the luminance values Y, respectively.

Figure 6:
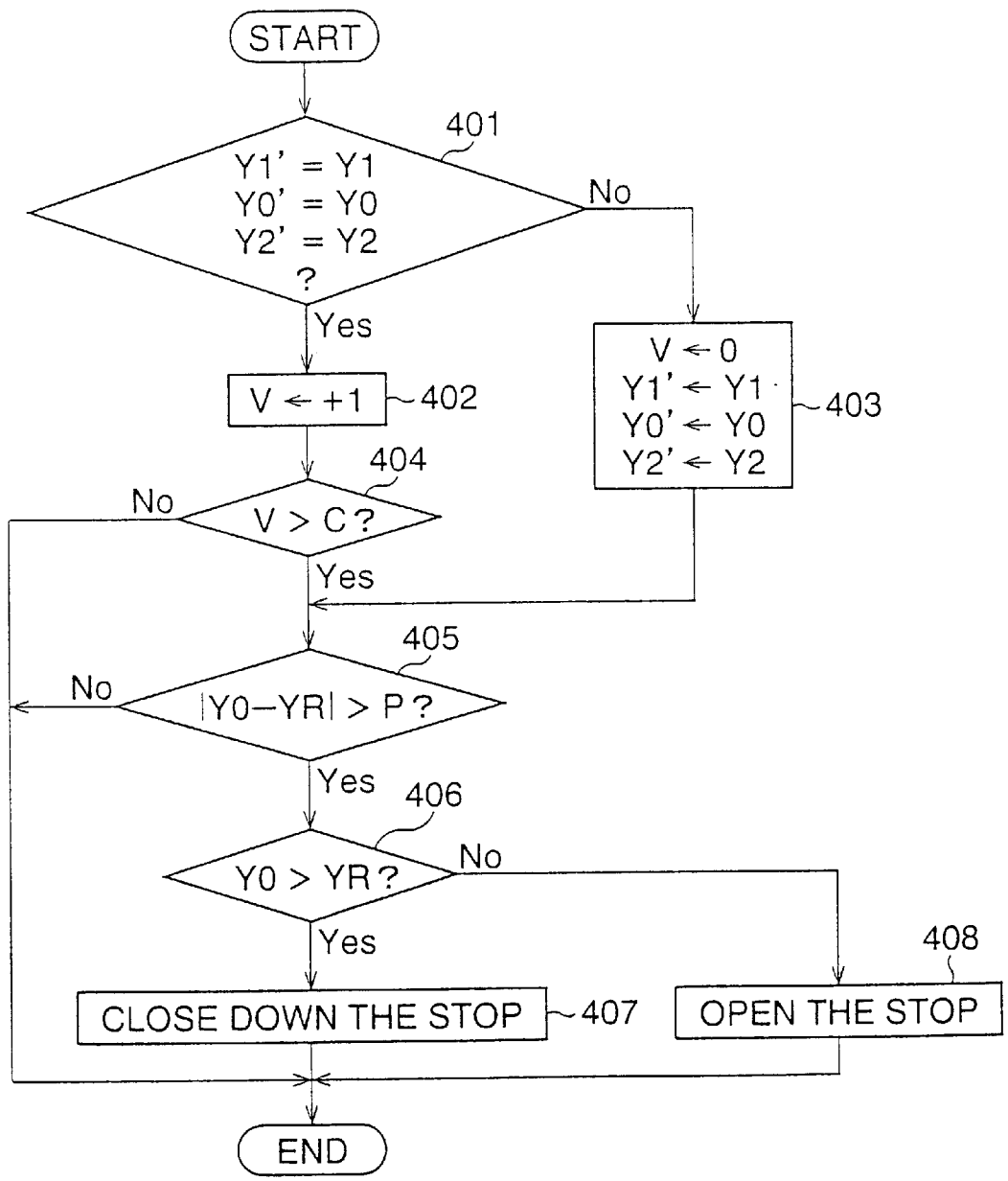
FIG. 6 is a flowchart showing the interrupt processing in detail.

FIG. 6 is a flowchart showing the control of the illuminating-light (shown in FIG. 3) in detail.

In Step 401, it is determined whether or not the maximum luminance value Y1, the average luminance value Y0, and the minimum luminance value Y2, are respectively equal to a last maximum luminance value Y1', a last average luminance value Y0', and a last minimum luminance value Y2'.

Note that, the last maximum luminance value Y1', the last average luminance value Y0' and the last minimum luminance value Y2' represent respectively a maximum value, an average value, and a minimum value, which were calculated by a preceding performance of Step 205, that is, Steps 301 to 303 (shown in FIG. 4). When the representative value (Y0, Y1, Y2) is not newly calculated because the histogram-data is not newly read by the CPU 22, the last maximum luminance value Y1', the last average luminance value Y0', and the last minimum luminance value Y2' are automatically regarded as the maximum luminance value Y1, the average luminance value Y0, and the minimum luminance value Y2, respectively.

In Step 401, when the maximum luminance value Y1, the average luminance value Y0, and the minimum luminance value Y2, are respectively equal to the last maximum luminance value Y1', the average luminance value Y0', and the minimum luminance value Y2', the process goes to Step 402.

In Step 402, a variable V is incremented by 1. The variable V is provided for counting a number of times which the maximum luminance value Y1, the average luminance value Y0, and the minimum luminance value Y2 are respectively equal to the last maximum luminance value Y1', the last average luminance value Y0', and the last minimum luminance value Y2'. Note that, initially, the variable V is set to 0.

Then, in Step 404, it is determined whether the variable V exceeds an allowance-constant C. When the variable V does not exceed the allowance-constant C, the stop 18 is not driven, in short, the control of the illuminating-light is not performed. When the variable V exceeds the allowance-constant C, the process goes to Step 405. In this embodiment, the allowance-constant C is predetermined to 4. Therefore, when a period in which the control of the illuminating-light is not performed exceeds 4/30 sec, the stop 18 is driven even if the representative value (Y0, Y1, Y2) is equal to a preceding representative value (Y0', Y1', Y2').

On the other hand, in Step 401, when the maximum luminance value Y1 is not equal to the last maximum luminance value Y1', or the average luminance value Y0 is not equal to the last average luminance value Y0', or the minimum luminance value Y2 is not equal to the last minimum luminance value Y2', the process goes to Step 403.

In Step 403, the variable V is set to 0, and then the last maximum luminance value Y1', the last average luminance value Y0', and the last minimum luminance value Y2' are respectively set to the maximum luminance value Y1, the average luminance value Y0, the minimum luminance value Y2. Step 403 is performed for the next control of the illuminating-light.

In Step 405, it is determined whether or not a difference |Y0−YR| between the average luminance value Y0 and a reference value YR is more than an allowance-value P. There reference value YR is an average luminance value, which can be calculated when the brightness of the object image formed on the image sensor 31 is proper. In this embodiment, the reference value YR is predetermined to 128. Namely, the reference value YR is predetermined to a middle value of the range of luminance values Y (from 0 to 255). On the other hand, the allowance-value P represents a permissible margin of error. In this embodiment, the allowance-error P is predetermined to 3. When the difference |Y0−YR| is not more than the allowance-value P (=3) the control of the illuminating-light is not performed, as the average luminance value Y0 is substantially equal to the reference value YR. When the difference |Y0−YR| is more than the allowance-value P (=3), the process goes to Step 406.

In Step 406, it is determined whether or not the average luminance value Y0 is more than the reference value YR. When the average luminance value Y0 is more than the reference value YR, step 407, is executed to close down stop 18. When the average luminance value Y0 is not more than the reference value YR, the stop 18 is opened at Step 408. When the stop 18 is opened or closed down, the interrupt processing, that is, the control of the illuminating-light is ended, and then the process returns to the main routine shown in FIG. 2.

As described above, when the representative value (Y1, Y0, Y2) is equal to the last representative value (Y1', Y0', Y2'), the control of the illuminating-light is not performed. Thus, the stop 18 is not driven on the basis of the last average luminance value Y0' calculated by a preceding performance of Steps 301 to 303. Therefore, the stop 18 is rapidly controlled without causing a hunting-situation, thus, the brightness of the object image formed on the image sensor 31, that is, the brightness of the object image displayed on the monitor 23 is always maintained at a proper level.

When the control of the illuminating-light is performed with comparing the representative value with the preceding representative value, as shown in Step 401, it is possible that, in some cases of white-balance adjustment processing, an improper brightness of the object image continues for a long time. This is because, in a case where the white-object is extremely bright or dark, the brightness of the object image does not change even though the stop 18 is driven a little, so that the representative value (Y0, Y1, Y2) does not change.

However, in the present embodiment, when the period in which the representative value (Y0, Y1, Y2) equals to the preceding representative value (Y0', Y1', Y2') exceeds $1/30$ sec, the stop 18 is driven, as shown in Steps 404. Thus, it never happens that the stop 18 remains not driven when the brightness of the object image is improper.

In this embodiment, the control routine of the illuminating-light is preformed at time-intervals of $1/30$ sec, to correspond to an NTSC Video Standard. When a PAL (Phase Alternation by Line) Video Standard method is applied as the color-television method, the control routine of the illuminating-light is performed at time-intervals of $1/25$ sec, according to a period of scanning of the object image ($=1/25$ sec). In this case, the maximum period in which the control of the illuminating-light is not performed is $4/25$ sec in place of $4/30$ sec.

In a modification, the representative value may be composed of only the average luminance value Y0.

Further, the representative value may be directly calculated on the basis of the luminance signals, without the histogram processing.

Finally, it will be understood by those skilled in the art that the foregoing description is of preferred embodiments of the device, and that various changes and modifications may be made to the present invention without departing from the spirit and scope thereof.

The present disclosure relates to subject matters contained in Japanese Patent Application No.10-308348 (filed on Oct. 29, 1998) which is expressly incorporated herein, by reference, in its entirety.

What is claimed is:

1. An electronic endoscope comprising:

a video-scope having an image sensor, provided at a distal end of said video-scope, on which an object image is formed;

a video-processor, to which a proximal end of said video-scope is connected, that processes image-pixel signals corresponding to said object image, successively read from said image sensor;

a light source provided in said video-processor such that light, emitted from said light source, is guided through said video-scope and radiates from the distal end of said video-scope;

a stop, provided between said light source and the proximal end of said video-scope, that adjusts a quantity of light radiating from the distal end of said video-scope;

a luminance generator that successively generates luminance signals from said image-pixel signals;

a calculator that successively calculates a representative value, associated with a brightness of said object image, on the basis of said luminance signals;

a light-controller that adjusts the brightness of said object image at regular time-intervals, by controlling said stop on the basis of said representative value and a predetermined reference value; and a determiner that determines whether said representative value coincides with a preceding representative value from a preceding calculation;

said light-controller not driving said stop when said representative value coincides with said preceding representative value and driving said stop when said representative value does not coincides with said preceding representative value.

2. The electronic endoscope of claim 1, wherein said representative value is composed of a maximum luminance value, a minimum luminance value, and an average luminance value of one frame worth of said luminance signals.

3. The electronic endoscope of claim 1, wherein said representative value is composed of an average luminance value of one frame worth of said luminance signals.

4. The electronic endoscope of claim 1, wherein said regular time-intervals depend on a period of scanning one frame worth of said object image.

5. The electronic endoscope of claim 4, wherein said regular time-intervals are one of time-intervals of $1/30$ sec, and time-intervals of $1/25$ sec.

6. The electronic endoscope of claim 1, wherein said light-controller drives said stop when a period in which said representative value coincides with said preceding representative value exceeds a predetermined time.

7. The electronic endoscope of claim 6, wherein said predetermined time is one of $4/30$ sec and $4/25$ sec.

8. The electronic endoscope of claim 1, wherein said predetermined reference value is predetermined to a middle of a range of luminance signals, such that the brightness of said object image formed on said image sensor is proper.

9. The electronic endoscope of claim 1, further comprising a histogram generator that generates histogram-data on the basis of said luminance signals, said calculator reading said histogram-data and then calculating said representative value on the basis of said histogram-data.

10. The electronic endoscope of claim 9, wherein said calculator does not calculate said representative value when said histogram-data can not be read from said histogram generator.

11. The electronic endoscope of claim 10, wherein said light-controller regards said preceding representative value as said representative value when said calculator does not calculate said representative value.

* * * * *